United States Patent
Patarin et al.

(10) Patent No.: US 7,923,398 B2
(45) Date of Patent: Apr. 12, 2011

(54) PREPARATION OF A POROUS COMPOSITE MATERIAL BASED ON EU-1 ZEOLITE AND ITS IMPLEMENTATION IN THE ISOMERIZATION OF $C_8$ AROMATICS

(75) Inventors: Joël Patarin, Flaxlanden (FR); Emmanuelle Guillon, Vernaison (FR); Loic Rouleau, Charly (FR); Simone Goergen, Lyons (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 157 days.

(21) Appl. No.: 12/203,546

(22) Filed: Sep. 3, 2008

(65) Prior Publication Data

US 2009/0062585 A1    Mar. 5, 2009

(30) Foreign Application Priority Data

Sep. 4, 2007    (FR) ..................... 07 06233

(51) Int. Cl.
*B01J 29/06*    (2006.01)
(52) U.S. Cl. ................ 502/60; 502/62; 502/63; 502/64; 502/74
(58) Field of Classification Search .................. 502/60, 502/62, 63, 64, 69, 74
See application file for complete search history.

(56) References Cited

U.S. PATENT DOCUMENTS

| | | | |
|---|---|---|---|
| 3,338,672 A * | 8/1967 | Haden, Jr. et al. ............ | 423/710 |
| 4,560,542 A * | 12/1985 | Robson .......................... | 423/703 |
| 6,004,527 A | 12/1999 | Murrell et al. | |
| 2002/0026657 A1 | 2/2002 | Bird | |
| 2003/0147805 A1* | 8/2003 | Koegler et al. ................ | 423/700 |
| 2004/0162454 A1* | 8/2004 | Gao et al. ...................... | 585/722 |

FOREIGN PATENT DOCUMENTS

| | | | |
|---|---|---|---|
| FR | 2 785 279 A | | 5/2000 |
| WO | WO 98/06495 | * | 2/1998 |
| WO | WO 99/16709 A | | 4/1999 |

OTHER PUBLICATIONS

Arnold A et al : "Dry-Gel Synthesis of Zeolites [A] EU-1 and [GA]EU-1" Microporous and Mesoporous Materials, Elsevier Science Publishing, New York, US vol. 67, No. 2-3 (Feb. 6, 2004) XP004485734.

Arnold A et al: "Insight Into the Dry-Gel Synthesis of Gallium-Rich Zeolite [GA]Beta" Microporous and Mesoporous Materials, Elsevier Science Publishing, New York, US vol. 62, No. 1-2, (Aug. 14, 2003) XP004441138.

Microporous and Mesoporous Materials 27 (1999) 95 106—"Preparation and catalytic testing of zeolite coatings on preshaped alumina supports" —N. van der Puil—pp. 95-106.

* cited by examiner

*Primary Examiner* — Elizabeth D Wood
(74) *Attorney, Agent, or Firm* — Millen, White, Zelano & Branigan, P.C.

(57) ABSTRACT

A preparation process is described for a porous composite material formed from an amorphous core based on at least one silicon oxide on which crystals of EU-1 zeolite are dispersed, said process comprising 1) the impregnation of a solid comprising a silicon oxide and an aluminum oxide with an aqueous solution comprising a hexamethonium cation, 2) the hydrothermal treatment, implemented in an autoclave of volume V (ml) under steam and at a temperature T comprised between 120 and 220° C., of said solid from stage 1), the quantity of water introduced beforehand into said autoclave being strictly greater than a volumetric quantity equal to $V*[23.48*10^{-10}*T^3 - 48*10^{-8}*T^2 + 5*10^{-5}*T - 0.002]$ and less than or equal to $0.25*V$, and is such that said solid is not in direct contact with it, 3) the drying then calcination of the solid from stage 2). The preparation a catalyst from said material for its use in the isomerization of $C_8$ aromatics is also described.

17 Claims, No Drawings

PREPARATION OF A POROUS COMPOSITE MATERIAL BASED ON EU-1 ZEOLITE AND ITS IMPLEMENTATION IN THE ISOMERIZATION OF $C_8$ AROMATICS

TECHNICAL FIELD

The present invention relates to the field of the preparation of a porous composite material comprising EU-1 zeolite crystals on its external surface and the application of said material for the isomerization of $C_8$ aromatic compounds. More precisely, the preparation of said material according to the invention uses the conversion to EU-1 zeolite of an amorphous and porous structure composed of one or more inorganic oxide(s). This conversion is carried out during a hydrothermal treatment carried out in the presence of a determined quantity of an external aqueous phase.

PRIOR ART

The EU-1 zeolite, of EUO structural type, is described in the prior art (W. M. Meier and D. H. Olson, "Atlas of Zeolite Structure types", 5th Edition, 2001) and has a mono-dimensional microporous network, the diameter of the pores of which is 4.1×5.4 Å (1 Å=1 Angström=1×10$^{-10}$ m). N. A. Briscoe et al have taught that these mono-dimensional channels have side pockets with a depth of 8.1 Å and a diameter of 6.8×5.8 Å (*Zeolites*, 8, 74, 1988).

European patent application EP-A-0,042,226 describes the EU-1 zeolite with the following formula:

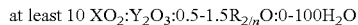

at least 10 $XO_2:Y_2O_3:0.5-1.5R_{2/n}O:0-100H_2O$ where R represents a cation of valency n, X represents silicon and/or germanium, Y represents at least one element chosen from aluminium, iron, gallium, boron. It also describes the process for the preparation of said EU-1 zeolite, which comprises the mixing in aqueous medium of at least one source of an element X, at least one source of an element Y and a nitrogen-containing organic compound that acts as a structuring agent Q, which is either the alkylated derivative of a α-ω diammonium polymethylene, or a degradation product of said derivative, or also precursors of said derivative. The reaction mixture is then placed under autogenous pressure, at a temperature comprised between 85 and 250° C., until zeolite crystals form. The product obtained is recovered by filtration, washed, dried, calcined in order to remove the organic structuring agent and optionally subjected to ion exchanges in order to obtain the acid form of the EU-1 zeolite. It is known to use the acid form of the EU-1 zeolite prepared in this way in a process for the isomerization of $C_8$ aromatic compounds. The EU-1 zeolite, prepared by the standard process described in European patent application EP-A-0,042,226, is obtained in the form of a powder and requires forming with a binder before being used as a catalyst. A hydrogenating metal is then deposited on the zeolite or/and on the binder. For example, U.S. Pat. No. 6,057,486 describes a catalyst for the isomerization of $C_8$ aromatic compounds and having 1 to 90% by weight of EU-1 zeolite mixed in a homogeneous manner with an inorganic binder, for example alumina, and having 0.01 to 20% by weight of at least one element of group VIII of the periodic table of the elements.

The homogenization of a zeolite powder with a matrix by the shaping techniques is a delicate operation. A more attractive alternative for forming catalysts is to directly deposit the zeolite crystals on a support during the stage of synthesizing the zeolite. Another advantage of such a procedure is that the use of a binder in order to fix the zeolite onto a support is no longer necessary.

Van der Puil et al. (Microporous and Mesoporous Materials 27 (1999) 95-106), for example, immersed alpha alumina supports in an aqueous solution containing all the reagents necessary for the formation of a zeolite. This mixture containing the inorganic supports is subjected to a hydrothermal treatment in order to allow the crystallization of the zeolite. The crystals formed settle on the surface of the support until the external surface of this support is completely covered.

Other processes for preparing catalysts by direct route during the synthesis of the zeolite implement the conversion to zeolite of reagents which have been shaped.

International patent application WO 99/16709 describes a preparation process which makes it possible to preserve some intercrystalline porosity in the zeolitic structure. A reactive and porous inorganic structure, for example a meso- and/or macroporous silicic structure, is used as reagent to form the zeolite. This structure is then impregnated whilst dry with aqueous solutions of other reagents necessary for the formation of a zeolite (structuring agent, mineralizing agent, framework element, etc.). The hydrothermal treatment is then carried out in the absence of a sufficient quantity of water, which could cause substantial surface gelation. The crystallization starts at the internal surface and then progresses through the whole structure. At least 15% of the starting inorganic structure is converted to zeolite. The macroscopic morphology of the initial structure is preserved and at least 25% of the porous volume is preserved.

SUMMARY AND BENEFIT OF THE INVENTION

The present invention relates to a process for the preparation of a porous composite material formed from an amorphous core based on at least one silicon oxide on which crystals of EU-1 zeolite are dispersed, said process comprising at least the following stages:

1) impregnation of a solid comprising at least one silicon oxide and at least one aluminium oxide with at least one aqueous solution comprising at least one quaternary diammonium cation of formula $[R_1R_2R_3—N—(CH_2)_n—N—R_4R_5R_6]^{2+}$, n being comprised between 3 and 12, $R_1$ to $R_6$, equal or different, are alkyl or hydroxyalkyl groups with 1 to 8 carbon atoms, and up to 5 of the $R_1$ to $R_6$ groups can be hydrogen atoms,
2) the hydrothermal treatment, implemented in an autoclave of volume V (ml) under steam and at a temperature T comprised between 120 and 220° C., of said solid from stage 1), the quantity of water introduced beforehand into said autoclave being strictly greater than a volumetric quantity equal to $V*[23.48*10^{-10}*T^3-48*10^{-8}*T^2+5*10^{-5}*T-0.002]$ and less than or equal to $0.25*V$, and is such that said solid is not in direct contact with it,
3) the drying then calcination of the solid from stage 2) so as to obtain said porous composite material.

The preparation of said material according to the invention implements the conversion to EU-1 zeolite of an amorphous and porous structure composed of one or more inorganic oxide(s). This conversion is carried out during said hydrothermal treatment carried out in the presence of a determined quantity of water. A crystallization phenomenon occurs first on an external surface of the solid before progressing, depending on the synthesis time, towards the inside of the solid. The synthesis is interrupted before the rate of conversion to EU-1 zeolite exceeds 15% by weight. The core of the material remains amorphous.

The present invention also relates to the preparation of a catalyst comprising said porous composite material, said catalyst also comprising at least one metal of group VIII of the periodic table of the elements. In accordance with the invention, the crystals of EU-1 zeolite are dispersed on the external surface of said core of said porous composite material and it is not necessary to use a binder to shape the zeolite which constitutes a valuable advantage for the preparation of the catalyst according to the invention. Said catalyst is advantageously used in a process for the isomerization of an aromatic fraction comprising at least one aromatic compound with eight carbon atoms per molecule. It was surprisingly discovered that such a catalyst, for example in the form of beads or of extrudates, comprising a porous composite material formed from an amorphous core on which EU-1 zeolite crystals are dispersed, leads to improved catalytic performances in terms of yield of xylenes when said catalyst is used in a process for the isomerization of an aromatic fraction comprising at least one aromatic compound with eight carbon atoms per molecule.

DESCRIPTION OF THE INVENTION

A subject of the present invention is a process for the preparation of a porous composite material formed from an amorphous core based on at least one silicon oxide on which EU-1 zeolite crystals are dispersed, said process comprising at least the following stages:

1) impregnation of a solid comprising at least one silicon oxide and at least one aluminium oxide with at least one aqueous solution comprising at least one quaternary diammonium cation of formula $[R_1R_2R_3—N—(CH_2)_n—N—R_4R_5R_6]^{2+}$, n being comprised between 3 and 12, $R_1$ to $R_6$, equal or different, are alkyl or hydroxyalkyl groups with 1 to 8 carbon atoms, and up to 5 of the $R_1$ to $R_6$ groups can be hydrogen atoms, 2) the hydrothermal treatment, implemented in an autoclave of volume V (ml) under steam and at a temperature T comprised between 120 and 220° C., of said solid from stage 1), the quantity of water introduced beforehand into said autoclave being strictly greater than a volumetric quantity equal to $V*[23.48*10^{-10}*T^3 - 48*10^{-8}*T^2 + 5*10^{-5}*T - 0.002]$ and less than or equal to $0.25*V$, and is such that said solid is not in direct contact with it, 3) the drying then calcination of the solid from stage 2) so as to obtain said porous composite material.

In accordance with the invention, the material prepared by the process of the invention is a porous composite material formed from an amorphous core based on at least one silicon oxide on which EU-1 zeolite crystals are dispersed. Said material thus obtained is in the main macroporous. It has wider pores and a pore volume at least 30% less than the pore volume of the solid comprising at least one silicon oxide and at least one aluminium oxide used for the implementation of said stage 1) of the process of the invention. The amorphous core of said material is formed from silicon oxide or from a mixture of silicon oxide and aluminium oxide, preferably, it is entirely constituted by silicon oxide. Crystals and agglomerates of crystals of EU-1 zeolite are dispersed on the external surface of said core without a continuous and crystallized layer of EU-1 zeolite entirely covering said surface. Said material is characterized by transmission electron microscopy (TEM) and by scanning electron microscopy (SEM). Said porous composite material prepared according to the process of the invention can be in different macroscopic forms, for example in the form of extrudates or beads, preferably in the form of extrudates. In accordance with the invention, said porous composite material is in the same macroscopic form as that of the solid comprising at least one silicon oxide and at least one aluminium oxide used for the implementation of said stage 1) of the process of the invention.

The solid comprising at least one silicon oxide and at least one aluminium oxide used for the implementation of stage 1) of the process for the preparation of the material according to the invention is for example an amorphous silica-alumina having an overall $SiO_2/Al_2O_3$ molar ratio of at least 10 and preferably comprised between 10 and 150. Said silica-alumina can be in different macroscopic forms, for example extrudates, beads or any other form known to a person skilled in the art. The average size of said silica-alumina can vary between 0.1 and 5 mm and preferably between 0.5 and 3 mm. It has an ordered or random porous system, comprising meso- and/or macropores, i.e. with an average pore diameter greater than 2 nm and a pore volume comprised between 0.01 and 2 $ml \cdot g^{-1}$ and preferably between 0.1 and 1.5 $ml \cdot g^{-1}$. In accordance with the invention, said porous composite material is in the same macroscopic form as that of the silica-alumina.

The solid comprising at least one silicon oxide and at least one aluminium oxide used for the implementation of stage 1) of the process for the preparation of the material according to the invention can also be obtained by impregnation of an aqueous solution containing aluminium on a structure constituted by at least silicon oxide. The silicon oxide used is a structure which can be in different macroscopic forms, for example extrudates, beads or any other form known to a person skilled in the art. The average diameter of said structure constituted by silicon oxide used can vary between 0.1 and 5 mm and preferably between 0.5 and 3 mm. Said structure constituted by silicon oxide has an ordered or random porous system, comprising meso- and/or macropores, i.e. with an average pore diameter greater than 2 nm and a pore volume comprised between 0.01 and 2 $ml \cdot g^{-1}$ and preferably between 0.1 and 1.5 $ml \cdot g^{-1}$.

According to the embodiment of impregnation of said aqueous solution containing aluminium on said silicon oxide structure, said solid comprising at least one silicon oxide and at least one aluminium oxide has either aluminium distributed homogeneously within the structure constituted by silicon oxide or aluminium deposited on the external surface of said structure constituted by silicon oxide.

In order to obtain a solid comprising at least one silicon oxide and at least one aluminium oxide having aluminium distributed homogeneously within the structure constituted by silicon oxide, the structure constituted by silicon oxide is impregnated at ambient temperature, whilst dry, in excess or according to any other method known to a person skilled in the art, with an aqueous solution comprising a source of aluminium. The preferred impregnation method is impregnation while dry and the volume of the aqueous solution containing aluminium to be impregnated is preferably equal to the pore volume of the structure constituted by silicon oxide.

After impregnation, said solid comprising at least one silicon oxide and at least one aluminium oxide having aluminium distributed homogeneously within the structure constituted by silicon oxide has an overall $SiO_2/Al_2O_3$ molar ratio of at least 10 and preferably comprised between 10 and 150.

In order to obtain a solid comprising at least one silicon oxide and at least one aluminium oxide having aluminium deposited on the external surface of said structure constituted by silicon oxide, the structure constituted by silicon oxide is firstly impregnated with a liquid free from aluminium. Preferably, an impregnation is carried out whilst dry, at ambient temperature, with a volume of liquid equal to or slightly less than the pore volume of the structure of silicon oxide. The pore volume of said structure constituted by silicon oxide is at least 90%, preferably between 95 and 99% filled with this liquid. The liquid free from aluminium and used to block the porosity of the structure constituted by silicon oxide is advantageously chosen from water, an organic solvent and a mixture of water and organic solvent. It is possible to use an alcohol, a compound comprising a quaternary ammonium function, an organic acid, a polyol as organic solvent or other solvents known to a person skilled in the art, said organic solvent having the property of decomposing between 100 and 1000° C. in order to be eliminated by calcination. Then said structure is impregnated, by impregnation whilst dry or in excess, preferably by impregnation whilst dry, with an aqueous solution of a source of aluminium. In this way, the diffusion of aluminium in the pores of the structure constituted by silicon oxide is reduced or even prevented and the aluminium is deposited in the main on the external surface of said structure. The solid comprising at least one silicon oxide and at least one aluminium oxide used for the implementation of said stage 1) of the process of preparation according to the invention has an overall $SiO_2/Al_2O_3$ molar ratio of at least 200. The porous composite material prepared according to the process of the invention and prepared from a solid having aluminium deposited on the external surface of said structure constituted by silicon oxide is characterized by an aluminium distribution coefficient of less than 0.5, preferably less than 0.4 and very preferably less than 0.3. Said aluminium distribution coefficient, obtained by a Castaing microprobe, corresponds to the ratio of the concentrations of aluminium in the core of an extrudate or of a bead of said porous composite material compared with that at the edge of this same extrudate or this bead according to the macroscopic form of said material.

In accordance with the invention, said porous composite material is in the same macroscopic form as that of the structure constituted by silicon oxide when said solid used for the implementation of Stage 1) is obtained by impregnation of an aqueous solution containing aluminium on said structure of silicon oxide.

The source of aluminium used for the impregnation on the structure constituted by silicon oxide can advantageously be any compound comprising aluminium and capable of releasing the aluminium in aqueous solution in reactive form. The source of aluminium is preferably sodium aluminate or an aluminium salt, for example chloride, nitrate, hydroxide or sulphate, or also an aluminium alkoxide.

After the impregnation of the aluminium, which is either distributed homogeneously within the structure constituted by silicon oxide or deposited on the external surface of said structure constituted by silicon oxide, said solid comprising silicon oxide and aluminium oxide is advantageously dried at a temperature below 200° C. and preferably below 120° C. and very preferably below 100° C. and/or advantageously calcined under air at a temperature comprised between 150° C. and 1000° C., preferably between 300° C. and 700° C. and still more preferably between 400° C. and 650° C. for a period of 1 hour to 20 hours.

In accordance with stage 1) of the preparation process according to the invention, said solid comprising at least one silicon oxide and at least one aluminium oxide is impregnated with at least one aqueous solution comprising at least one quaternary diammonium cation Q of formula $[R_1R_2R_3-N-(CH_2)_n-N-R_4R_5R_6]^{2+}$, n being comprised between 3 and 12, $R_1$ to $R_6$, equal or different, are alkyl or hydroxyalkyl groups with 1 to 8 carbon atoms, and up to 5 of the $R_1$ to $R_6$ groups can be hydrogen atoms. Preferably, n is equal to 6, $R_1$, $R_2$, $R_3$, $R_4$, $R_5$ and $R_6$ are methyl groups: this is the hexamethonium cation. The impregnation of said solid containing silicon and aluminium oxides is carried out at ambient temperature, whilst dry, in excess or according to any other method known to a person skilled in the art, with an aqueous solution comprising at least said quaternary diammonium cation Q. The preferred method of impregnation is impregnation whilst dry and the volume of the aqueous solution comprising at least said cation Q to be impregnated is less than or equal to the pore volume of the solid comprising at least one silicon oxide and at least one aluminium oxide. Said cation Q is present in hydroxide form or as a halogenated salt, preferably in hydroxide form. Very preferably, said aqueous solution comprising said cation Q comprises hexamethonium hydroxide.

The impregnation of the aqueous solution comprising said quaternary diammonium cation Q is advantageously repeated several times, for example three impregnations are carried out. After each impregnation stage a drying is carried out at a temperature below 200° C. and preferably below 120° C. and very preferably below 100° C. in order to evaporate the water and free the pore volume for a successive impregnation.

At the end of the impregnation and drying stage(s) according to said stage 1) of the process of the invention, the solid has the following molar composition:

| | |
|---|---|
| $SiO_2/Al_2O_3$ | at least 10, |
| $OH^-/SiO_2$ | 0.1 to 6.0, preferably 0.1 to 1.0, |
| $(M + Q)/Al_2O_3$ | 0.5 to 100, |
| $Q/(M + Q)$ | 0.1 to 1, |
| $H_2O/SiO_2$ | 0 to 20, |

M represents a monovalent cation, originating from the sources of silicon and aluminium, chosen from the alkali metals and ammonium. Preferably, M is sodium.

In accordance with stage 2) of the preparation process according to the invention, said solid from said stage 1) and containing at least the silicon and aluminium oxides is subjected to a hydrothermal treatment, implemented in an autoclave of volume V (ml) under steam and at a temperature T comprised between 120 and 220° C., so as to lead to the formation of crystals of EU-1 zeolite, dispersed on the surface of said solid. According to said stage 2), the quantity of water introduced beforehand into said autoclave is strictly greater than a volume equal to $V*[23.48*10^{-10}*T^3-48*10^{-8}*T^2+5*10^{-5} T-0.002]$ and is less than or equal to a volume equal to $0.25*V$ and is such that said solid is not in direct contact with the water.

For the implementation of said stage 2) of the process of the invention, said solid from stage 1) of the process of the invention is advantageously placed on a stainless support, located in the upper or central part of an autoclave. At the bottom of this autoclave water is present which is not in direct contact with said solid. The quantity of water introduced at the bottom of the autoclave is chosen such that it is sufficient for the atmosphere around said solid to be saturated with steam and for the water to re-condense on said solid. The volume of water introduced at the bottom of the autoclave is strictly greater than a volume equal to $V*[23.48*10^{-10}*T^3-48*10^{-8}*T^2+5*10^{-5} T-0.002]$ and is less than or equal to a volume equal to $0.25*V$, V being the volume of the autoclave expressed in ml and T the temperature of the hydrothermal treatment expressed in ° C. Preferably, the hydrothermal treatment is carried out at a temperature of 180° C. in a 100-ml autoclave, the quantity of water introduced at the bottom of the autoclave and not in direct contact with the solid is greater than 0.5 ml, preferably at least equal to 1 ml and still more preferably at least equal to 4 ml. The water which re-condenses on the solid causes a gelation of the external surface of said solid, such that a crystallization phenomenon occurs, which starts at the external surface of said solid before progressing, according to the synthesis time, to the inside of the solid. The "surface gelation" corresponds, within the meaning of the present invention, to a significant dissolution, at the surface, of the inorganic solid accompanied by a loss of surface porosity and by the formation, also at the surface, of a denser amorphous phase. The core is less affected by the surface gelation phenomenon such that its porosity is less modified than that at the surface during the crystallization. In accordance with the invention, the external surface gelation phenomenon occurs in a manner such that the core of the porous composite material prepared according to the process of the invention remains amorphous, the gelation of the external surface creating a diffusion barrier which limits the progression of the crystallization of the external surface towards the core. No crystallization phenomenon in the core of said material is observed, the crystals of EU-1 zeolite only being present on the external surface of said amorphous core.

The hydrothermal treatment, carried out for the implementation of said stage 2) of the process of the invention, is carried out under an autogenous reaction pressure, at a temperature comprised between 120° C. and 220° C., preferably between 140° C. and 200° C., and very preferably at a temperature comprised between 150 and 190° C. The synthesis duration is from 1 hour to several days, preferably, from 6 hours to 7 days and still more preferably from 12 hours to 4 days. The synthesis is advantageously stopped when the level of conversion to EU-1 zeolite is less than or equal to 15% by weight, preferably less than or equal to 10% by weight. The level of conversion is at least 1% by weight, preferably at least 4% by weight, at the surface and is less than 3% by weight and preferably less than 1% by weight in the core of the material.

The rate of conversion to EU-1 zeolite is determined by X-ray diffraction relative to a reference sample entirely constituted by 100% crystalline EU-1 zeolite. More precisely, it is calculated from the diffraction diagram of the porous composite material prepared according to the process of the invention by comparison with that of said reference sample entirely constituted by 100% crystalline EU-1 zeolite. Said reference sample is constituted by an EU-1 zeolite prepared according to the teaching described in the patent application EP A-0,042,226 and which is 100% crystalline. The rate of conversion, expressed in % by weight, corresponds to the ratio of the surface area of the peaks of the porous composite material prepared according to the process of the invention on the surface of the peaks of the 100% crystallized reference EU-1 zeolite, after subtraction of the background noise from the field of the angle of diffraction 2θ from 13° to 32°.

At the end of said stage 2) of the preparation process according to the invention, the material obtained is in its raw synthesis form. It is recovered, washed, then in accordance with stage 3) of the preparation process according to the invention, it is dried, preferably at a temperature below 200° C. and very preferably below 120° C. then it is calcined. The calcination is carried out by the methods known to a person skilled in the art, for example under a flow of dry air in order to eliminate the quaternary diammonium cation Q acting as organic structuring agent occluded in the micropores of the material. The calcination is advantageously carried out at a temperature comprised between 150° C. and 1000° C., more advantageously comprised between 300° C. and 700° C. and still more advantageously comprised between 400° C. and 650° C. for a period preferably comprised between 1 hour and 40 hours and more preferably comprised between 10 and 20 hours. If the calcined material contains $M^+$ cations in the form of cations of alkali metals, at least one stage of ion exchange is carried out, for example with at least one aqueous solution of $NH_4NO_3$, in order to eliminate at least some and preferably all of the cations of alkali metals.

A subject of the present invention is also the preparation of a catalyst from the porous composite material prepared in accordance with the process of the invention described above. Said process for the preparation of said catalyst comprises at least one stage involving the impregnation of said porous composite material with at least one metal of group VIII of the periodic table of the elements and optionally at least one metal chosen from the metals of groups IIIA and IVA.

The preparation of the catalyst according to the invention, after the preparation of the material in accordance with the three stages of preparation of the process described above, can be carried out by any method known to a person skilled in the art. Preferably, following the calcination carried out at the end of stage 3) of the process for the preparation of the material according to the invention and any stages of ion exchange, for example with an aqueous solution of $NH_4NO_3$, at least one metal of group VIII is introduced onto said material, namely either mostly into the core, or mostly onto the crystals of EU-1 zeolite or also onto the zeolite-core core combination. The deposition of said metal on the core is advantageously carried out by the technique of impregnation whilst dry, the technique of impregnation in excess or by ion exchange. When several metals are introduced, the latter can be introduced either all in the same manner or by different techniques.

All the precursors of metals of group VIII are suitable for the deposition of one or more metal(s) of group VIII on the material prepared according to the process of the invention in three stages described above. In particular, for any noble metal of group VIII, it is possible to use ammonia compounds or compounds such as for example ammonium chloroplatinate, dicarbonyl platinum dichloride, hexahydroxyplatinic acid, palladium chloride or palladium nitrate. The platinum is generally introduced in the form of hexachloroplatinic acid. The introduction of the noble metal of group VIII is preferably carried out by impregnation using an aqueous or organic solution of one of the metal compounds mentioned above. Among the organic solvents which can be used, there can be mentioned the paraffinic, naphthenic or aromatic hydrocarbons containing for example 6 to 12 carbon atoms per molecule, and the halogenated organic compounds containing for example 1 to 12 carbon atoms per molecule. There can be mentioned for example n-heptane, methylcyclohexane, toluene and chloroform. It is also possible to use mixtures of solvents.

The checking of certain parameters implemented during the deposition, in particular the nature of the precursor of the metal(s) of group VIII used, makes it possible to direct the deposition of said metal(s) mostly to the core of the material prepared according to the process of the invention or to the zeolite crystals.

Thus, in order to introduce the metal(s) of group VIII, preferably platinum and/or palladium, mostly onto the core, an anion exchange with hexachloroplatinic acid and/or hexachloropalladic acid can be implemented, in the presence of a competitive agent, for example hydrochloric acid, the deposition being in general followed by a calcination, for example at a temperature comprised between 350 and 550° C. and for a period comprised between 1 and 4 hours. With such precursors, the metal(s) of group VIII is (are) deposited mostly on the core and said metal(s) has (have) a good dispersion and a good macroscopic distribution through the extrudates or the beads of the catalyst.

It is also possible to envisage depositing the metal(s) of group VIII, preferably platinum and/or palladium, by cation exchange such that said metal(s) is (are) deposited mostly on the zeolite crystals. Thus, in the case of platinum, the precursor can be for example chosen from:

ammonia compounds such as tetramine platinum (II) salts of formula $Pt(NH_3)_4X_2$, hexamine platinum (IV) salts of formula $Pt(NH_3)_6X_4$; salts of halogenopentamine platinum (IV) of formula $(PtX(NH_3)_5)X_3$; salts of N-tetrahalogenodiamine platinum of formula $PtX_4(NH_3)_2$; and the halogenated compounds of formula $H(Pt(acac)_2X)$;

X being a halogen chosen from the group formed by chlorine, fluorine, bromine and iodine, X preferably being chlorine, and "acac" representing the acetylacetonate group (of total formula $C_5H_7O_2$), derived from acetylacetone. With such precursors, the metal(s) of group VIII is (are) deposited mostly on the zeolite crystals and said metal(s) has (have) a good dispersion and a good macroscopic distribution through the catalyst extrudates or beads.

The impregnation whilst dry of the metal of group VIII on the material leads to the deposition of said metal both on the core and on the zeolite crystals.

Preferably, the technique of impregnation whilst dry will be used, in order to promote the deposition of the metal of group VIII in a crust of the porous composite material prepared according to the process of the invention in three stages described above: the macroscopic distribution coefficient of said metal(s) of group VIII, calculated from the distribution profile of said metal(s) of group VIII determined by a Castaing microprobe, is less than 0.7, preferably less than 0.6. Said coefficient is defined as the ratio of the concentrations of said metal(s) of group VIII in the core of an extrudate or bead of the catalyst compared with that at the edge of this same extrudate or this same bead according to the macroscopic form of said catalyst.

In the case where the catalyst prepared according to the invention also contains at least one metal chosen from the metals of groups IIIA and IVA, all the techniques of deposition of such a metal known to a person skilled in the art and all the precursors of such metals may be suitable.

It is possible to add the metal(s) of group VIII and that (those) of groups IIIA and IVA, either separately or simultaneously in at least one unitary stage. When at least one metal of groups IIIA and IVA is added separately, it is preferable for it to be added after the metal of group VIII.

The additional metal chosen from the metals of groups IIIA and IVA can be introduced via compounds such as for example the chlorides, the bromides and the nitrates of the metals of groups IIIA and IVA. For example in the case of indium, the nitrate or chloride is advantageously used. The additional metal chosen from the metals of groups IIIA and IVA can also be introduced in the form of at least one organic compound chosen from the group constituted by the complexes of said metal, in particular the polyketone complexes of the metal and the hydrocarbyl metals such as the metal alkyls, cycloalkyls, aryls, alkylaryls and arylalkyls. In this latter case, the introduction of the metal is advantageously carried out using a solution of the organometallic compound of said metal in an organic solvent. It is also possible to use organohalogenated compounds of the metal. As organic compounds of metals, there can be mentioned in particular tetrabutyl tin, in the case of tin, and triphenylindium, in the case of indium.

If the additional metal chosen from the metals of groups IIIA and IVA is introduced before the metal of group VIII, the compound of the IIIA or IVA metal used is generally chosen from the group constituted by the halide, nitrate, acetate, tartrate, carbonate and oxalate of the metal. The introduction is then advantageously carried out in aqueous solution. But it can also be introduced using a solution of an organometallic compound of the metal, for example tetrabutyl tin. In this case, before introducing at least one metal of group VIII, a calcination under air will be carried out.

Moreover, intermediate treatments such as for example a calcination and/or a reduction can be applied between the successive depositions of the different metals.

The preparation of the catalyst generally concludes with a calcination, usually at a temperature comprised between 250° C. and 600° C., for a period comprised between 0.5 and 10 hours, preferably preceded by drying, for example in an oven, at a temperature ranging from ambient temperature to 250° C., preferably from 40° C. to 200° C. Said drying stage is preferably carried out during the rise in temperature necessary for carrying out said calcination. The calcination is optionally followed by reduction under hydrogen, generally at a temperature comprised between 300 and 600° C., preferably between 350° C. and 550° C., and for a period comprised between 1 and 10 hour(s), preferably between 2 and 5 hours, so as to obtain said metal(s) chiefly in the reduced form necessary for the catalytic activity.

In the case where the catalyst prepared according to the present invention contains sulphur, the sulphur is introduced onto the calcined catalyst, containing the element(s) mentioned previously, either in situ before the catalytic reaction, or ex situ. The sulphurization is carried out using any sulphurizer well known to a person skilled in the art, such as for example dimethyl disulphide or hydrogen sulphide. Any sulphurization occurs after the reduction. In the case of in situ sulphurization, the reduction, if the catalyst has not been reduced beforehand, occurs before the sulphurization. In the case of ex situ sulphurization, the reduction is carried out, then the sulphurization.

The catalyst thus prepared contains, apart from an amorphous core on which EU-1 zeolite crystals are dispersed, at least one metal of group VIII of the periodic table of the elements, preferably chosen from the group formed by platinum and palladium, still more preferably platinum. The content by weight of said metal(s) of group VIII is generally comprised between 0.01 and 2.0%, preferably between 0.05 and 1.0%. Said catalyst optionally comprises at least one additional metal chosen from the metals of groups IIIA and IVA of the periodic table of the elements, preferably chosen from indium and tin. The content by weight of said additional metal(s) is generally comprised between 0.01 and 2.0%, preferably between 0.05 and 1.0%. Said catalyst also advantageously comprises sulphur, the level of which is such that the ratio of the number of sulphur atoms to the number of atoms of metal of group VIII deposited is comprised between 0.5 and 2.

A subject of the present invention is also a process of isomerization of a fraction containing at least one aromatic compound with eight carbon atoms per molecule, said process comprising the bringing of said aromatic fraction into contact with at least said catalyst prepared according to said process described above and present in a catalytic reactor. Said aromatic fraction containing at least one aromatic compound having eight carbon atoms per molecule comprises in particular as aromatic compound having eight carbon atoms per molecule either only a mixture of xylenes, or only ethylbenzene or a mixture of xylene(s) and ethylbenzene.

The catalyst used in the process of isomerization of the $C_8$ aromatic fractions according to the present invention is in the form of beads or extrudates.

Said isomerization process is generally implemented according to the following operating conditions:

- a temperature comprised between 300° C. and 500° C., preferably between 320° C. and 450° C. and still more preferably between 340° C. and 430° C.,
- a partial hydrogen pressure comprised between 0.3 and 1.5 MPa, preferably between 0.4 and 1.2 MPa and still more preferably between 0.7 and 1.2 MPa,
- a total pressure comprised between 0.45 and 1.9 MPa, preferably between 0.6 and 1.5 MPa,
- a feed space velocity, expressed in kilograms of charge introduced per kilogram of catalyst and per hour, comprised between 0.25 and 30 $h^{-1}$, preferably between 1 and 10 $h^{-1}$, and still more preferably between 2 and 6 $h^{-1}$.

The following examples illustrate the invention without however limiting its scope. The materials prepared in the following examples 1 to 6 are characterized by X-ray diffraction (Panalytical, X'Pert), by scanning electron microscopy (JEOL, JSM 6340), by transmission electron microscopy (FEI, Tecnai) and by Castaing microprobe (JEOL, 8800R).

The reference sample entirely constituted by EU-1 zeolite, used in the following examples, is prepared according to the teaching described in patent application EP A-0,042,226 and is 100% crystalline.

Example 1 (Invention)

Preparation of a Porous Composite Material M1 Containing 5% by Weight EU-1 Zeolite As porous and amorphous structure, 7 g of extrudates of silica supplied by the company Saint Gobain N or Pro are taken, which have an average diameter of 1.5 mm, a pore volume of 1 $mL \cdot g^{-1}$ and an average pore diameter of 10 nm.

These extrudates of silica are then impregnated whilst dry and at ambient temperature with a solution comprising 0.55 g of sodium aluminate (Carlo Erba) in 7 mL of distilled water. The impregnated extrudates are then calcined under air at 500° C. for 2 hours.

An aqueous solution of hexamethonium hydroxide is prepared, by reacting 6 g of hexamethonium bromide (Acros) with 4.6 g of silver oxide (Alfa Aesar) in 12 g of distilled water. This mixture is left under stirring overnight shielded from the light. After separation of the AgBr precipitate by filtration, a solution of 25% by mass of hexamethonium hydroxide is recovered.

The extrudates are then impregnated whilst dry and at ambient temperature with 11 g of this solution of hexamethonium hydroxide. This impregnation is carried out in 3 stages. After each impregnation, the extrudates are dried at 80° C., in order to evaporate the water and free the pore volume.

At the end of these impregnation and drying stages, the extrudates have the following molar composition:

| | |
|---|---|
| $SiO_2/Al_2O_3$ | 40 |
| $OH^-/SiO_2$ | 0.2 |
| $(Na + HM)/Al_2O_3$ | 7; HM being hexamethonium |
| $HM/(Na + HM)$ | 0.6 |
| $H_2O/SiO_2$ | 0.8 |

The extrudates are then transferred to a stainless support located in the central part of an stainless 100-mL (V) autoclave. At the bottom of the autoclave, 5 mL of distilled water is introduced.

The hydrothermal treatment is carried out without stirring for a period of 1 day at 180° C. (T) by introduction of the autoclave into a 50-L Binder ventilated oven.

The product is recovered, washed with distilled water (500 mL) and dried at 100° C. It is then calcined under air at 550° C. for 18 hours. The material M1 is obtained.

An X-ray diffraction analysis, by comparison with a reference sample entirely constituted by EU-1 zeolite, shows that the material M1 comprises 5% by weight of EU-1 zeolite corresponding to a rate of conversion of 5% by weight. By scanning electron microscopy analysis, a dispersion of crystalline aggregates of EU-1 zeolite measuring 1 to 5 μm is observed on the external surface of the extrudates of the material M1, whilst the breaking of an extrudate reveals a core which has the same morphology as the initial silica extrudate. Transmission electron microscopy analyses carried out on samples taken from the surface and core of the extrudates of the material M1 show that the surface is composed of crystalline particles which diffract the electron beam whilst the sample taken from the core is amorphous. The material M1 is also analyzed by Castaing microprobe: analyses are carried out stepwise all along the internal section of an extrudate of the material M1. The distribution coefficient of the aluminium, denoted R(A1), is equal to 1.

Example 2 (Invention)

Preparation of a Porous Composite Material M2 Containing 15% by Weight EU-1 Zeolite This material is prepared according to the operating method described in Example 1, but the hydrothermal treatment is carried out for 2 days at 180° C. At the end of the preparation, the material M2 is obtained.

An X-ray diffraction analysis by comparison with a reference sample entirely constituted by EU-1 zeolite shows that the material M2 comprises 15% by weight EU-1 zeolite corresponding to a rate of conversion of 15% by weight. Through a scanning electron microscope analysis, crystalline aggregates of EU-1 zeolite measuring 1 to 10 μm are observed on the external surface of the extrudates and around the periphery over a thickness of approximately 100 μm, whilst the fracture of an extrudate reveals a core which has the same morphology as the initial silica extrudate. Transmission electron microscopy analyses carried out on samples taken from the surface and from the core of the extrudates of the material M2 show that the surface is composed of crystalline particles which diffract the electron beam whilst the sample taken from the core is amorphous. The material M2 is also analyzed by Castaing microprobe: analyses are carried out stepwise all along the internal section of an extrudate of the material M2. The distribution coefficient of the aluminium, denoted R(A1), is equal to 1.

Example 3 (Invention)

Preparation of a Porous Composite Material M3 Containing 5% by Weight EU-1 Zeolite As porous and amorphous structure, 7 g of extrudates of silica supplied by the company Saint Gobain N or Pro are taken, which have an average diameter of 1.5 mm, a pore volume of 1 $mL*g^{-1}$ and an average pore diameter of 10 nm.

These extrudates of silica are then impregnated whilst dry and at ambient temperature with 6.8 g of a solution of hexamethonium hydroxide at 25% by mass prepared according to the procedure described in Example 1. These extrudates are then impregnated whilst dry and at ambient temperature with a solution comprising 0.03 g of sodium aluminate (Carlo Erba) in 1 ml of distilled water. The impregnated extrudates are then calcined under air at 500° C. for 2 hours.

The extrudates are then impregnated whilst dry and at ambient temperature with 11 g of a solution of hexamethonium hydroxide at 25% by mass. This impregnation is carried out in 3 stages. After each impregnation, the extrudates are dried at 80° C. in order to evaporate the water and free pore volume.

At the end of these impregnation and drying stages, the extrudates have the following molar composition:

| | |
|---|---|
| $SiO_2/Al_2O_3$ | 731 |
| $OH^-/SiO_2$ | 0.2 |
| $(Na + HM)/Al_2O_3$ | 78; HM being hexamethonium |
| $HM/(Na + HM)$ | 1.0 |
| $H_2O/SiO_2$ | 0.8 |

The extrudates are then transferred to a stainless support located in the central part of a stainless 100-mL (V) autoclave. At the bottom of the autoclave, 5 mL of distilled water is introduced.

The hydrothermal treatment is carried out without stirring for a period of 1 day at 180° C. (T) by introduction of the autoclave into a ventilated 50-L Binder oven.

The product is recovered, washed with distilled water (500 mL) and dried at 100° C. It is then calcined under air at 550° C. for 18 hours. The material M3 is obtained.

An X-ray diffraction analysis by comparison with a reference sample entirely constituted by EU-1 zeolite shows that the material M3 comprises 5% by weight EU-1 zeolite corresponding to a rate of conversion of 5% by weight. Through a scanning electron microscope analysis, a dispersion of crystalline aggregates of EU-1 zeolite measuring 1 to 5 μm is observed on the external surface of the extrudates of said material M3 whilst the fracture of an extrudate reveals a core which has the same morphology as the initial silica extrudate. Transmission electron microscopy analyses carried out on samples taken from the surface and from the core of the extrudates of the material M3 show that the surface is composed of crystalline particles which diffract the electron beam whilst the sample taken from the core is amorphous. The material M3 is also analyzed by Castaing microprobe: analyses are carried out stepwise all along the internal section of an extrudate of the material M3, The distribution coefficient of the aluminium, denoted R(A1), is equal to 0.2.

Example 4 (Invention)

Preparation of a Porous Composite Material M4 Containing 15% by Weight EU-1 Zeolite As porous and amorphous structure, 7 g of extrudates of silica supplied by the company Saint Gobain N or Pro are taken, which have an average diameter of 1.5 mm, a pore volume of 1 mL·g$^{-1}$ and an average pore diameter of 10 nm.

These extrudates of silica are firstly impregnated whilst dry and at ambient temperature with 6.8 g of a solution of hexamethonium hydroxyl at 25% by mass prepared according to the procedure described to Example 1. These extrudates are then impregnated whilst dry and at ambient temperature with a solution comprising 0.08 g of sodium aluminate (Carlo Erba) in 1 mL of distilled water. The impregnated extrudates are then calcined at 500° C. for 2 hours.

The extrudates are then impregnated whilst dry and at ambient temperature with 11 g of a solution of hexamethonium hydroxyl at 25% by mass. This impregnation is carried out in 3 stages. After each impregnation, the extrudates are dried at 80° C. in order to evaporate the water and free pore volume.

At the end of these impregnation and drying stages, the extrudates have the following molar composition:

| | |
|---|---|
| $SiO_2/Al_2O_3$ | 274 |
| $OH^-/SiO_2$ | 0.2 |
| $(Na + HM)/Al_2O_3$ | 30; HM being hexamethonium |
| $HM/(Na + HM)$ | 0.9 |
| $H_2O/SiO_2$ | 0.8 |

The extrudates are then transferred to a stainless support located in the central part of a stainless 100-mL (V) autoclave. At the bottom of the autoclave, 5 mL of distilled water is introduced.

The hydrothermal treatment is carried out without stirring for a period of 2 days at 180° C. (T) by introduction of the autoclave into a ventilated 50-L Binder oven.

The product is recovered, washed with distilled water (500 mL) and dried at 100° C. It is then calcined under air at 550° C. for 18 hours. The material M4 is obtained.

An X-ray diffraction analysis by comparison with a reference sample entirely constituted by EU-1 zeolite shows that the material M4 comprises 15% by weight EU-1 zeolite corresponding to a rate of conversion of 15% by weight. Through a scanning electron microscopy analysis, crystalline aggregates of EU-1 zeolite measuring 1 to 10 μm are observed on the external surface of the extrudates and around the periphery over a thickness of approximately 100 μm, whilst the fracture of an extrudate reveals a core which has the same morphology as the initial silica extrudate. Transmission electron microscopy analyses carried out on samples taken from the surface and from the core of the extrudates of the material M4 show that the surface is composed of crystalline particles which diffract the electron beam whilst the sample taken from the core is amorphous. The material M4 is also analyzed by Castaing microprobe: analyses are carried out stepwise all along the internal section of an extrudate of the material M4. The distribution coefficient of the aluminium, denoted R(A1), is equal to 0.4.

Example 5 (Comparative)

Preparation of a Porous Composite Material M5 Containing 15% by Weight EU-1 Zeolite This material is prepared according to the operating method described in Example 1, but the hydrothermal treatment is carried out, without introduction of distilled water at the bottom of the autoclave, for 3 days at 180° C. At the end of the preparation, the material M5 is obtained. An X-ray diffraction analysis by comparison with a reference sample shows that the material M5 comprises 15% by weight EU-1 zeolite corresponding to a rate of conversion of 15% by weight. Through a scanning electron microscope analysis, the formation of small crystalline particles of EU-1 zeolite measuring approximately 200 nm is observed on the external surface as well as in the core of the extrudates. Transmission electron microscopy analyses carried out on samples taken from the surface and from the core of the extrudates of the material M5 show that the surface and core samples are composed of crystalline particles which diffract the electron beam. The material M5 is also analyzed by Castaing microprobe: analyses are carried out stepwise all along the internal section of an extrudate. The distribution coefficient of the aluminium, denoted R(Al), is equal to 1.

Example 6 (Comparative)

Preparation of a Porous Composite Material M6 Containing 15% by Weight EU-1 Zeolite This material is prepared according to the operating method described in Example 1, but the hydrothermal treatment is carried out with introduction of 0.5 mL of distilled water at the bottom of the autoclave, for 3 days at 180° C. At the end of the preparation, the material M6 is obtained.

An X-ray diffraction analysis by comparison with a reference sample shows that the material M6 comprises 15% by weight EU-1 zeolite corresponding to a rate of conversion of 15% by weight. Through a scanning electron microscope analysis, the formation of small crystalline particles measuring approximately 200 nm is observed on the external surface as well as in the core of the extrudates. Transmission electron microscopy analyses carried out on samples taken from the surface and from the core of the extrudates of the material M5 show that the surface and core samples are composed of crystalline particles which diffract the electron beam. The material M5 is also analyzed by Castaing microprobe: analyses are carried out stepwise all along the internal section of an extrudate. The distribution coefficient of the aluminium, denoted R(Al), is equal to 1.

Example 7

Preparation of Catalysts C1 to C6

The materials M1 to M6, calcined, prepared according to Examples 1 to 6 are subjected to 3 ion exchanges in a solution of 10N NH$_4$NO$_3$ at 100° C. for 4 hours per exchange. After these treatments, the EU-1 zeolite comprised in these calcined materials is in the form NH$_4$.

The materials M1 to M6 are then impregnated whilst dry with hexachloroplatinic acid, in order to introduce onto each of the catalysts C1 to C6 a content by mass of platinum equal to 0.6%. The solids are finally dried at 120° C. for 12 hours and calcined under air at 500° C. for 1 hour. Thus the catalysts C1, C2, C3, C4, C5 and C6 are obtained, which are prepared respectively from the materials M1, M2, M3, M4, M5 and M6. The distribution coefficient of the platinum, determined by Castaing microprobe, is 0.4 for each of the catalysts C1 to C6.

Example 8

Evaluation of the Catalytic Properties of the Catalysts C1 to C6 in Isomerization of the C$_8$ Aromatics The charge to be isomerized, brought into contact successively with each of the catalysts C1 to C6, is constituted solely by ethylbenzene.

The performances of the catalysts C1 to C6 from Example 7 are evaluated in isomerization of ethylbenzene and using 5 g of catalyst.

The isomerization operating conditions are the following:
temperature: 410° C.;
total pressure: 10 bar (1 bar=0.1 MPa);
partial hydrogen pressure: 8 bar.
charge: ethylbenzene
feed space velocity, expressed in grams of charge introduced per gram of zeolite present in the catalyst (C1 to C6) and per hour, equal to 66.6 h$^{-1}$.

The catalysts containing 15% by weight of zeolite are tested at a space velocity, expressed per gram of charge introduced per gram of catalyst (C2, C4, C5 and C6) and per hour, equal to 10 h$^{-1}$. The catalysts containing 5% by weight of zeolite are tested to a space velocity, expressed by gram of charge introduced per gram of catalyst (C1 and C3) and per hour, equal to 3.33 h$^{-1}$. The performances of the catalysts C1 to C6 tested at the same charge flow rate per quantity of zeolite are therefore comparable. The catalytic properties of the catalysts C1 to C6 are successively evaluated for the isomerization of the ethylbenzene.

The catalysts are firstly reduced for 2 hours at 400° C. under hydrogen then they are treated with a charge containing dimethyldisulphide (DMDS) in the presence of hydrogen with a concentration such that the sulphur/metal atomic ratio is 1.5. The catalysts are kept for 3 hours at 400° C. in a flow of hydrogen, then the charge is injected.

The materials are evaluated in terms of isomerization yield. The yield in terms of xylenes (or also isomerization yield) is determined from the % by mass values of the xylenes produced, said percentages by mass being obtained by chromatographic analysis of the effluents.

TABLE 1 performances of the catalysts C1 to C6 in terms of yield of xylenes.

| | catalyst | | | | | |
|---|---|---|---|---|---|---|
| | C1 (invention) | C2 (invention) | C3 (invention) | C4 (invention) | C5 (comparative) | C6 (comparative) |
| % by weight EU-1 zeolite | 5 | 15 | 5 | 15 | 15 | 15 |
| R(Al) (Castaing microprobe) | 1 | 1 | 0.2 | 0.4 | 1 | 1 |
| Yield of xylenes (%) | 22.8 | 22.1 | 24.9 | 24.3 | 17.3 | 19.0 |

The results presented in Table 1 show that the catalysts C1, C2, C3 and C4 comprising a porous composite material formed from an amorphous core on which zeolite crystals EU-1 are dispersed lead to much better catalytic performances in terms of yield of xylenes than those obtained by means of the catalysts C5 and C6 comprising a porous composite material the core of which is not amorphous due to the presence of EU-1 zeolite crystals.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 07/06.233, filed Sep. 4, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the preparation of a porous composite material formed from an amorphous core based on at least one silicon oxide and at least one aluminum oxide on which crystals of EU-1 zeolite are dispersed on the external surface of said core without a continuous and crystallized layer of EU-1 zeolite entirely covering said surface, said process comprising at least the following stages in succession:
   1) impregnation and drying in at least one cycle of a reactive amorphous and porous solid comprising at least one silicon oxide and at least one aluminium oxide with at least one aqueous solution comprising at least one quaternary diammonium cation of formula $[R_1R_2R_3-N-(CH_2)_n-N-R_4R_5R_6]^{2+}$, n being comprised between 3 and 12, $R_1$ to $R_6$, equal or different, are alkyl or hydroxyalkyl groups with 1 to 8 carbon atoms, and up to 5 of the $R_1$ to $R_6$ groups can be hydrogen atoms,
   2) hydrothermal treatment, directly of resultant solid from stage 1) implemented in an autoclave of volume V (ml) under steam and at a temperature T comprised between 120 and 220° C., of said solid from stage 1), the quantity of water introduced beforehand into said autoclave being strictly greater than a volumetric quantity equal to $V*[23.48*10^{-10}*T^3-48*10^{-8}*T^2+5*10^{-5}*T-0.002]$ and less than or equal to $0.25*V$, and is such that said solid is not in direct contact with the water, and terminating the process before the rate of conversion to EU-1 zeolite exceeds 15% by weight, and wherein the asterisk* denotes a multiplication sign,
   3) drying then calcination of the solid from stage 2) so as to obtain said porous composite material having a dispersed layer of EU-1 crystals on the amorphous core without a continuous and crystallized layer of EU-1 zeolite entirely covering the surface of the core.

2. A preparation process according to claim 1 such that said amorphous core is formed from a mixture of silicon oxide and aluminium oxide.

3. A preparation process according to claim 1 wherein said porous composite material is in the form of extrudates.

4. A preparation process according to claim 1 wherein said solid comprising at least one silicon oxide and at least one aluminium oxide used for the implementation of said stage 1) is an amorphous silica-alumina having an overall $SiO_2/Al_2O_3$ molar ratio comprised between 10 and 150.

5. A preparation process according to claim 1 wherein said solid comprising at least one silicon oxide and at least one aluminium oxide used for the implementation of said stage 1) is obtained by impregnation of a solution containing a source of aluminium oxide on at least one structure constituted by silicon oxide.

6. A preparation process according to claim 5 wherein said solid comprising at least one silicon oxide and at least one aluminium oxide for the implementation of said stage 1) has aluminium oxide distributed homogeneously within said structure constituted by silicon oxide.

7. A preparation process according to claim 5 wherein said solid comprising at least one silicon oxide and at least one aluminium oxide for the implementation of said stage 1) has aluminium oxide deposited on the external surface of said structure.

8. A preparation process according to claim 7 wherein said porous composite material has an aluminium oxide distribution coefficient of less than 0.5.

9. A preparation process according to claim 5 wherein said porous composite material is in the same macroscopic form as that of said structure constituted by silicon oxide.

10. A preparation process according to claim 1 wherein said quaternary diammonium cation Q has a formula in which n is equal to 6 and $R_1$, $R_2$, $R_3$, $R_4$, $R_5$ and $R_6$ are methyl groups.

11. A preparation process according to claim 1 wherein each stage of impregnation according to said stage 1) is followed by a drying at a temperature below 200° C.

12. A preparation process according to claim 1 wherein at the end of said stage 1), the solid has the following molar composition:

| | |
|---|---|
| $SiO_2/Al_2O_3$ | at least 10, |
| $OH^-/SiO_2$ | 0.1 to 6.0, |
| $(M + Q)/Al_2O_3$ | 0.5 to 100, M representing a monovalent cation chosen from the alkali metals and ammonium, |
| $Q/(M + Q)$ | 0.1 to 1 |
| $H_2O/SiO_2$ | 0 to 20. |

13. A preparation process according to claim 1 wherein said hydrothermal treatment is carried out at a temperature of 180° C. in a 100-ml autoclave, the quantity of water introduced at the bottom of the autoclave and not in direct contact with the solid being at least equal to 4 ml.

14. A preparation process according to claim 1 wherein the synthesis is stopped when the rate of conversion to EU-1 zeolite is less than or equal to 10% by weight.

15. A process for the preparation of a catalyst comprising impregnating a porous composite material prepared according to the process according to claim 1 with at least one metal of group VIII of the periodic table of the elements.

16. A process for the preparation of a catalyst according to claim 15 wherein said metal(s) of group VIII is(are) deposited by impregnation while dry.

17. A process for the preparation of a catalyst according to claim 15 comprising subjecting the impregnated composite material to a stage of calcination comprised between 250° C. and 600° C. for a period comprised between 0.5 and 10 hours.

* * * * *